(12) United States Patent
Uenaka

(10) Patent No.: US 7,767,809 B2
(45) Date of Patent: Aug. 3, 2010

(54) CRYSTAL OF INTERMEDIATE FOR CARBAPENEM

(75) Inventor: Masaaki Uenaka, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 1113 days.

(21) Appl. No.: 10/542,810

(22) PCT Filed: Feb. 12, 2004

(86) PCT No.: PCT/JP2004/001477

§ 371 (c)(1),
(2), (4) Date: Mar. 1, 2006

(87) PCT Pub. No.: WO2004/072073

PCT Pub. Date: Aug. 26, 2004

(65) Prior Publication Data

US 2006/0229285 A1    Oct. 12, 2006

(30) Foreign Application Priority Data

Feb. 14, 2003    (JP) .............................. 2003-036233

(51) Int. Cl.
*C07D 477/20* (2006.01)
(52) U.S. Cl. .................................................... 540/350
(58) Field of Classification Search ................. 540/350
See application file for complete search history.

(56) References Cited

U.S. PATENT DOCUMENTS

| | | | |
|---|---|---|---|
| 5,317,016 A | 5/1994 | Nishitani et al. | 514/210 |
| 5,539,102 A | 7/1996 | Sendo et al. | 540/310 |
| 5,703,243 A | 12/1997 | Nishitani et al. | 548/541 |
| 2008/0171864 A1* | 7/2008 | Uenaka et al. | 540/204 |

FOREIGN PATENT DOCUMENTS

| | | |
|---|---|---|
| EP | 0 528 678 A1 | 2/1993 |
| EP | 0 528 678 B1 | 5/2001 |
| JP | 05-294970 | 11/1993 |

* cited by examiner

*Primary Examiner*—Mark L Berch
(74) *Attorney, Agent, or Firm*—Renner, Otto, Boisselle & Sklar, LLP

(57) ABSTRACT

The disclosed invention relates to a solvate of the compound (I) of the formula:

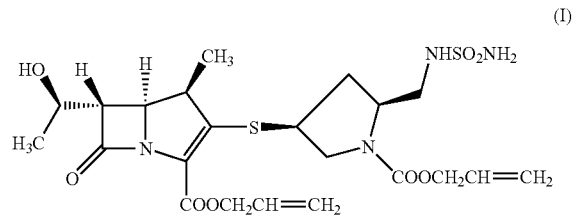

Figure 1:
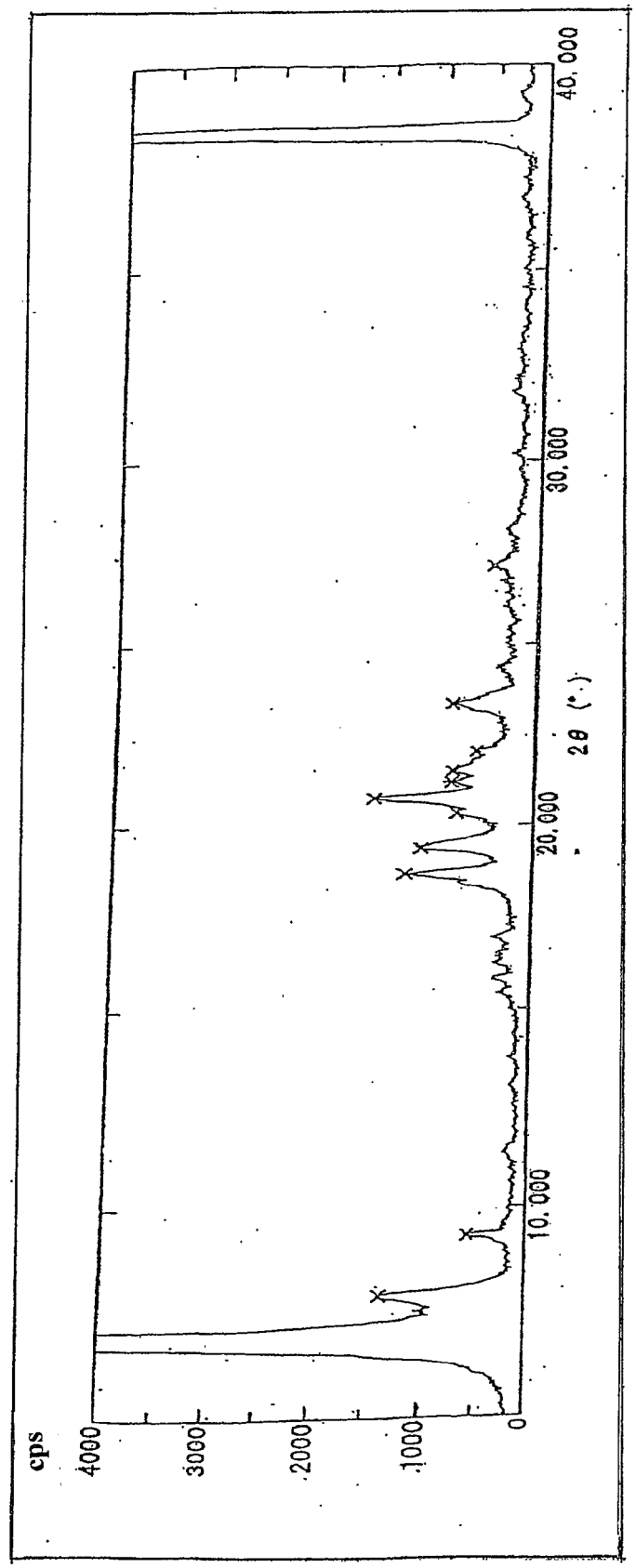

or a crystal thereof.

9 Claims, 5 Drawing Sheets

CRYSTAL OF INTERMEDIATE FOR CARBAPENEM

TECHNICAL FIELD

The present invention relates to solvates and crystals of carbapenem derivatives, which are useful intermediates to produce β-lactam antibiotics, and methods for producing them.

BACKGROUND ART

Pyrrolidinylthio carbapenem derivatives with a broad antibacterial spectrum (the below compound II) are known as useful antibiotics (see, Patent Document 1). The compound (I) of the present invention is a synthetic intermediate and described in Patent Document 1, but has not been isolated as a specific crystal form. Especially in an industrial manufacturing method, preferred is that a compound produced in each process has high purity or is isolated and purified as a crystal form which is easy to handle. However, a crystal of the compound (I) has not been isolated. Additionally, a method for producing the compound (II) with high purity by deprotecting a crystal of the compound (I) with high quality has not been reported. A crystal of the compound (II) and a method for producing thereof is known (see, Patent Document 2).

(Patent Document 1) Japanese Patent Publication (Kokai) 1993-294970

(Patent Document 2) International Publication WO 95/29913

DISCLOSURE OF INVENTION

Problems to be Solved by the Invention

The present invention is to dissolve the above problems and the object is to provide the compound (I), a solvate or a crystal thereof, having a superior stability for preservation, handling or the like, as well as a method for producing them and a method for producing the compound (II) by using the solvate or the crystal.

Means to Solve the Problems

The present inventors have intensively studied with considering the above situation and examined the solvation and crystallization with various kinds of combination of a dissoluble solvent (e.g., ethyl acetate) and an indissoluble solvent (e.g., alcohol such as 2-propanol), to accomplish the following present invention.

1. A solvate of the compound (I) of the formula:

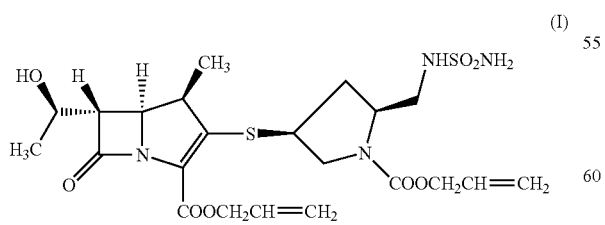

(I)

or a crystal thereof.

2. An alcohol solvate of the compound (I) or a crystal thereof according to the above 1.

3. A 2-propanol solvate of the compound (I) or a crystal thereof according to the above 1.

4. The crystal according to the above 3 wherein the content of 2-propanol is 0.1 to 2 moles per mole of the compound (I).

5. The crystal according to the above 3 wherein the content of 2-propanol is 0.5 mole per mole of the compound (I).

6. The crystal according to any one of the above 1 to 5 which has a powder X-ray diffraction pattern whose characteristic peaks appear as the spacing (d) of 12.80, 11.21, 4.75, 4.58, 4.28 angstrom.

7. A 2-pentanol solvate of the compound (I) or a crystal thereof according to the above 1.

8. The crystal according to the above 7 which has a powder X-ray diffraction pattern whose characteristic peaks appear as the spacing (d) of 14.77, 10.25, 5.36, 5.03, 4.66, 4.42, 4.25, 4.14, 4.05, 3.97, 3.62 angstrom.

9. A 1-pentanol solvate of the compound (I) or a crystal thereof according to the above 1.

10. The crystal according to the above 9 which has a powder X-ray diffraction pattern whose characteristic peaks appear as the spacing (d) of 12.13, 5.66, 4.98, 4.83, 4.56, 4.43, 4.21, 4.14, 3.76 angstrom.

11. A t-amyl alcohol solvate of the compound (I) or a crystal thereof according to the above 1.

12. The crystal according to the above 11 which has a powder X-ray diffraction pattern whose characteristic peaks appear as the spacing (d) of 14.72, 10.25, 5.36, 5.04, 4.79, 4.66, 4.43, 4.25, 4.06 angstrom.

13. A 1-propanol solvate of the compound (I) or a crystal thereof according to the above 1.

14. The crystal according to the above 13 which has a powder X-ray diffraction pattern whose characteristic peaks appear as the spacing (d) of 12.91, 4.78, 4.58 angstrom.

15. A method for producing the compound according to any one of the above 1 to 14 which comprises dissolving the compound (I) or the solvate in a dissoluble solvent and adding an indissoluble solvent thereto.

16. The method according to the above 15 which comprises dissolving the compound (I) or the solvate in ethyl acetate and adding an alcohol thereto.

17. A method for producing the compound (II) of the formula:

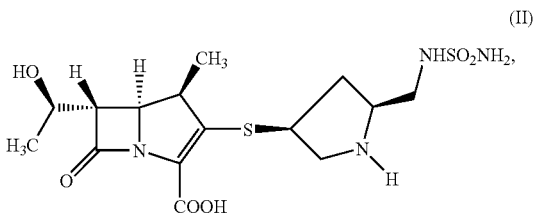

(II)

a solvate or a crystal thereof, comprising a process to deprotect a solvate of the compound (I) or a crystal thereof according to any one of the above 1 to 14.

18. The method according to the above 17, which comprises obtaining a crystal of the compound (I) or the solvate by the method according to the above 15 or 16 and deprotecting the crystal.

19. The method according to the above 17 or 18 which is a method for producing 1 hydrate crystal of the compound (II).

BRIEF DESCRIPTION OF THE DRAWINGS (FIG. 1) The figure shows the result of powder X-ray diffraction analysis of a crystal of a 2-propanol solvate of Example 2.

Figure 2:
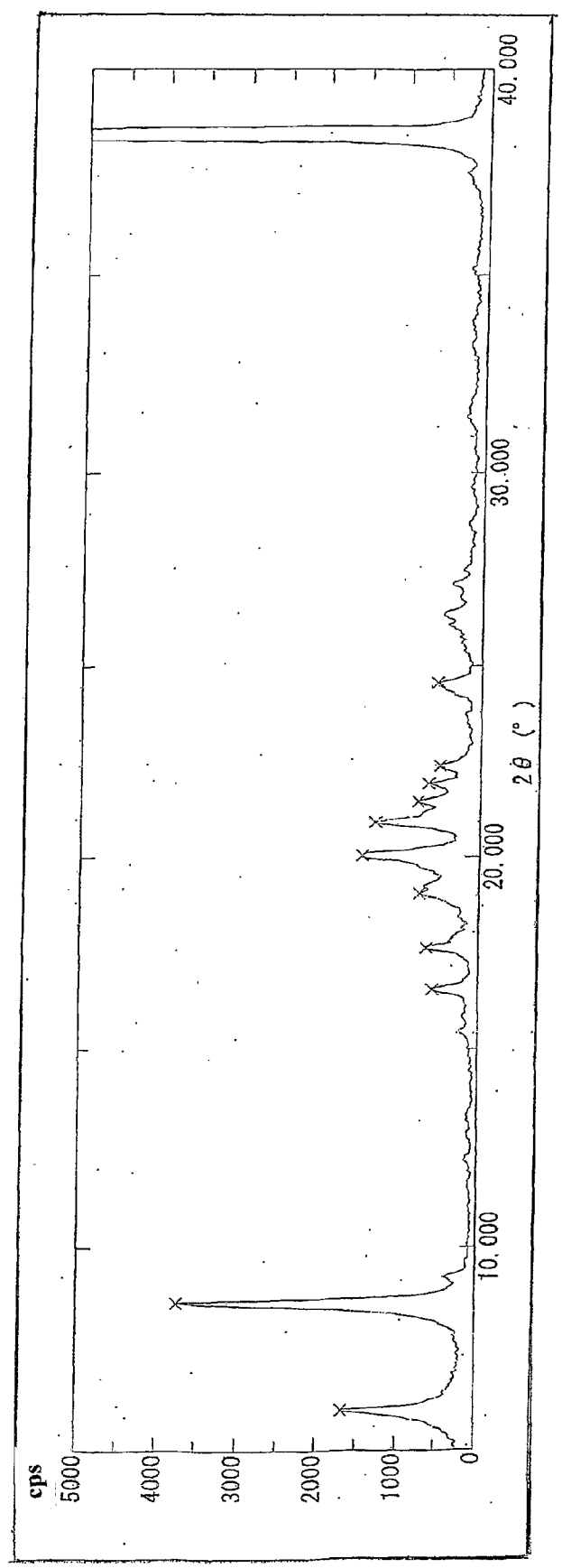

(FIG. 2) The figure shows the result of powder X-ray diffraction analysis of a crystal of a 2-pentanol solvate of Example 7.

Figure 3:
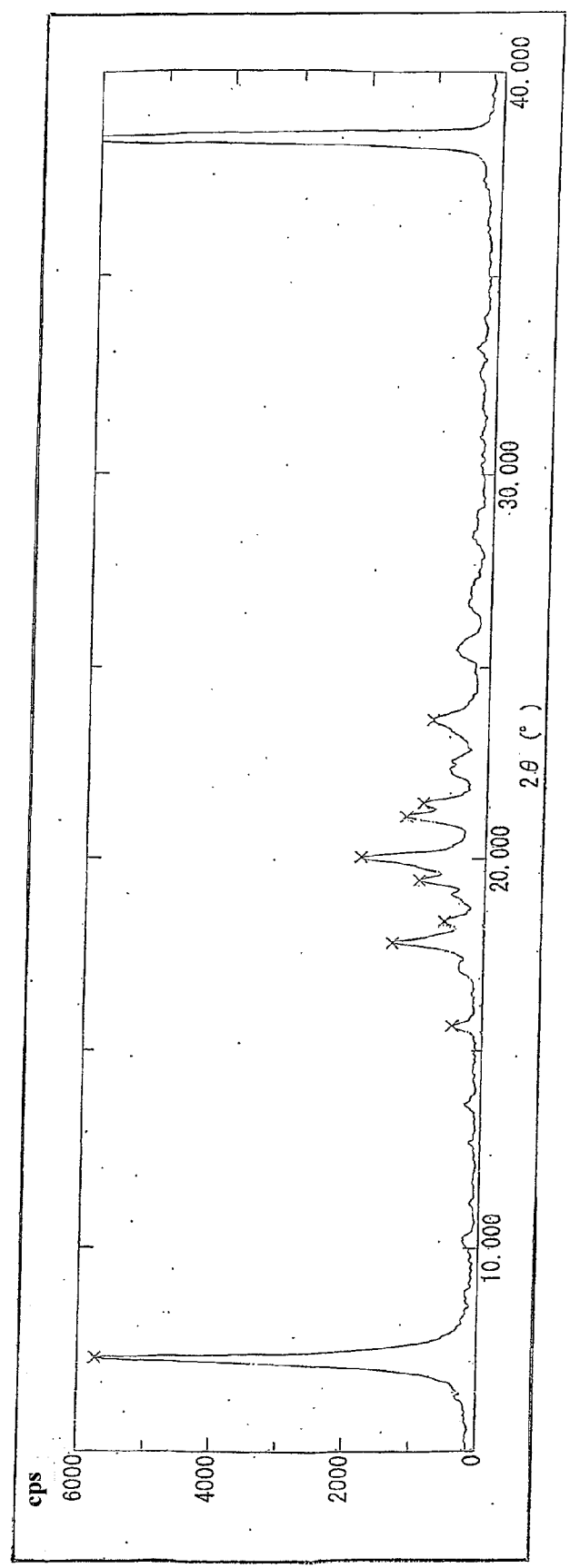

(FIG. 3) The figure shows the result of powder X-ray diffraction analysis of a crystal of a 1-pentanol solvate of Example 8.

Figure 4:
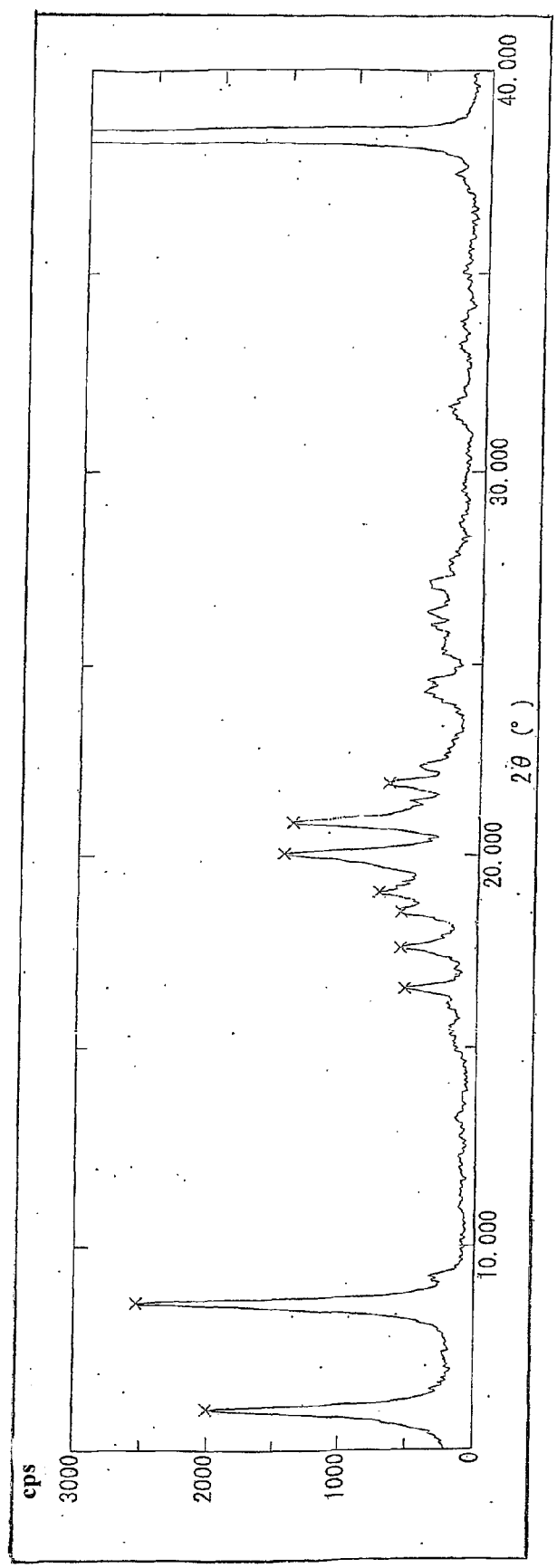

(FIG. 4) The figure shows the result of powder X-ray diffraction analysis of a crystal of a t-amyl alcohol solvate of Example 9.

Figure 5:
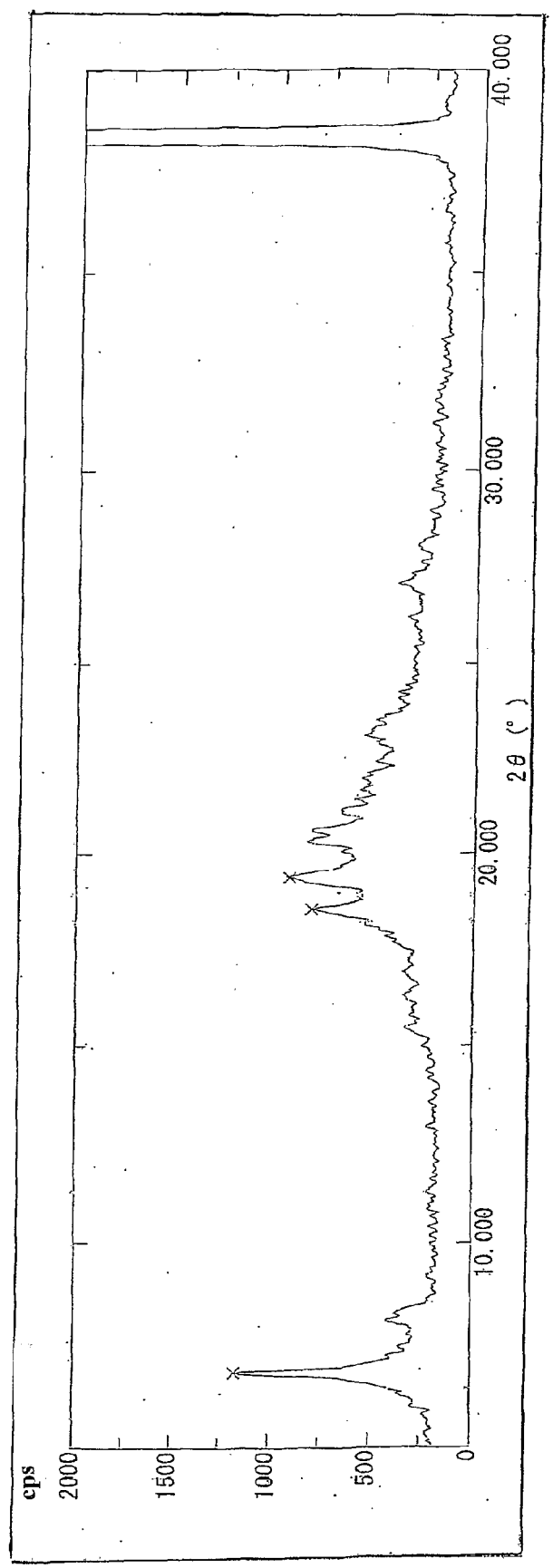

(FIG. 5) The figure shows the result of powder X-ray diffraction analysis of a crystal of a 1-propanol solvate of Example 10.

BEST MODE FOR CARRYING OUT THE INVENTION (1) A Solvate of the Compound (I) or a Crystal Thereof A solvate of the compound (I) in the present invention is preferably an alcohol solvate. An alcohol is, for example, preferably a C1 to C10 alcohol, more preferably a C3 to C5 alcohol, and especially preferably 2-propanol, 2-pentanol, 1-pentanol, t-amyl alcohol, 1-propanol or the like. The alcohol solvate preferably has a crystal form and more preferably shows a powder X-ray diffraction pattern of the below Tables 1 to 5 (Each corresponds to the FIGS. 1 to 5). In preferable embodiments, a crystal of a 2-propanol solvate shows a powder X-ray diffraction pattern of Table 1, a crystal of a 2-pentanol solvate shows the pattern of Table 2, a crystal of a 1-pentanol solvate shows the pattern of Table 3, a crystal of a t-amyl alcohol solvate shows the pattern of Table 4, or a crystal of a 1-propanol solvate shows the pattern of Table 5. Additionally, the content of each solvent is preferably 0.1 to 1 mole per mole of the compound (I). More preferred is that the content of a 2-propanol solvent is 0.5 mole per mole of the compound (I), the content of a 2-pentanol solvent is 0.25 mole, the content of a 1-pentanol solvent is 0.7 mole, the content of a t-amyl alcohol is 0.25 mole, or the content of a 1-propanol is 0.6 mole. Considering the handling such as crystallinity, a preferable crystal is a crystal of a 2-pentanol solvate or a crystal of a t-amyl alcohol solvate.

TABLE 1

| 2 θ (°) | d(Å) | Relative Intensity (%) |
|---|---|---|
| 6.90 | 12.80 | 100 |
| 7.88 | 11.21 | 8 |
| 9.32 | 9.48 | 4 |
| 18.66 | 4.75 | 7 |
| 19.36 | 4.58 | 7 |
| 20.32 | 4.37 | 5 |
| 20.76 | 4.28 | 9 |
| 21.18 | 4.19 | 5 |
| 21.50 | 4.13 | 5 |

TABLE 1-continued

| 2 θ (°) | d(Å) | Relative Intensity (%) |
|---|---|---|
| 22.02 | 4.03 | 4 |
| 23.34 | 3.81 | 5 |
| 27.14 | 3.28 | 3 |

TABLE 2

| 2 θ (°) | d(Å) | Relative Intensity (%) |
|---|---|---|
| 5.98 | 14.77 | 13 |
| 8.62 | 10.25 | 29 |
| 16.54 | 5.36 | 5 |
| 17.62 | 5.03 | 5 |
| 19.04 | 4.66 | 6 |
| 20.06 | 4.42 | 12 |
| 20.92 | 4.24 | 11 |
| 21.46 | 4.13 | 6 |
| 21.92 | 4.05 | 5 |
| 22.38 | 3.97 | 4 |
| 24.56 | 3.62 | 5 |

TABLE 3

| 2 θ (°) | d(Å) | Relative Intensity (%) |
|---|---|---|
| 7.28 | 12.13 | 70 |
| 15.64 | 5.66 | 6 |
| 17.80 | 4.98 | 17 |
| 18.36 | 4.83 | 8 |
| 19.44 | 4.56 | 13 |
| 20.04 | 4.43 | 23 |
| 21.10 | 4.21 | 15 |
| 21.46 | 4.14 | 12 |
| 23.64 | 3.76 | 11 |

TABLE 4

| 2 θ (°) | d(Å) | Relative Intensity (%) |
|---|---|---|
| 6.0 | 14.72 | 25 |
| 8.62 | 10.25 | 32 |
| 16.54 | 5.36 | 7 |
| 17.60 | 5.04 | 8 |
| 18.52 | 4.79 | 8 |
| 19.04 | 4.66 | 10 |
| 20.04 | 4.43 | 19 |
| 20.86 | 4.25 | 18 |
| 21.90 | 4.06 | 9 |

TABLE 5

| 2 θ (°) | d(Å) | Relative Intensity (%) |
|---|---|---|
| 6.84 | 12.91 | 13 |
| 18.54 | 4.78 | 9 |
| 19.38 | 4.58 | 10 |

(The X-ray diffraction condition: Tube CuKα radiation, Tube Voltage 40 Kv, Tube Current 30 mA, d sin θ=nλ (n is an integer, θ is a diffraction angle))

The above d-spacing values are calculated based on characteristic peaks with the strong relative intensity selected from the X-ray peaks and so a crystal structure is not necessarily determined by only these values. Namely, the other peaks can be comprised in the X-ray peaks. Furthermore, in a general X-ray analysis of a crystal, the peak has a few errors depending on a measuring equipment, a measuring condition, the presence of attached solvent or the like. For example, a d-spacing value may include an error of ±0.2 or so. The error of ±0.01 to ±0.1 or so may be occurred even though a very precise equipment is used. Therefore, a few errors should be considered when a crystal structure is identified, and all crystals characterized by a substantially same X-ray pattern as the above are within the scope of the present invention.

The method for producing a crystal of the present invention is explained in detail below.

The compound (I) itself is a well-known compound and, for example, can be produced by a reaction of the enol phosphate (III) with the 2-side chain thiol (IV) as shown below.

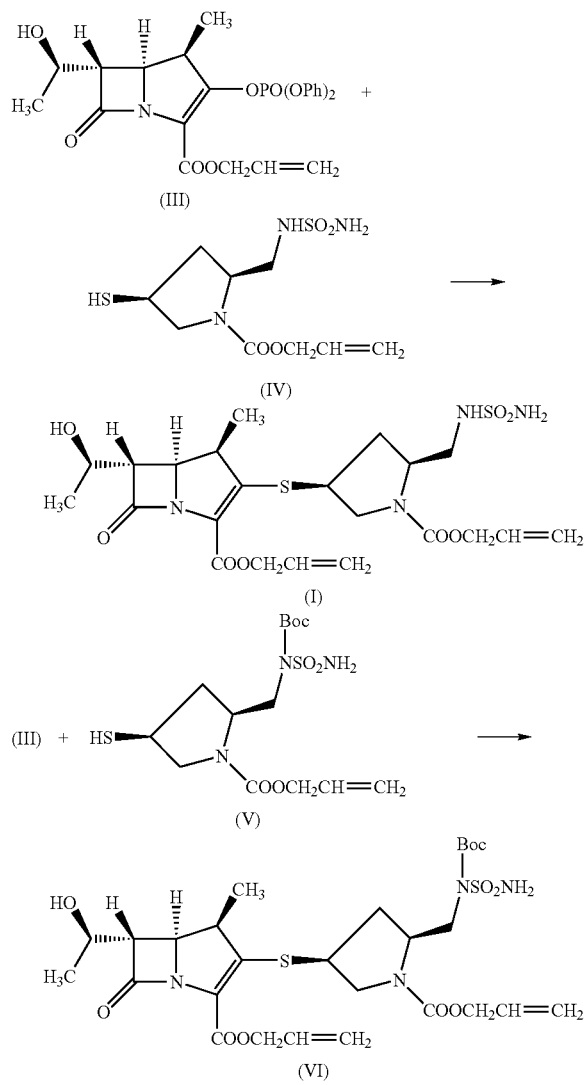

(wherein Ph is phenyl; Boc is t-butoxycarbonyl)

For example, the compound (I) can be produced by that the compound (III) is reacted with the compound (IV) in a solvent such as methylene chloride, acetonitrile, dimethylformamide or dimethylsulfoxide, in the presence of a base such as diisopropylethylamine, triethylamine or 4-dimethylaminopyridine. The reaction is carried out at about −20 to 40° C. for about 1 to 50 hours. After the reaction, the reaction solution is treated and concentrated. The residue is subjected to silica gel column chromatography or the like to obtain the compound (I) as powder. Alternatively, the compound (I) can be produced by a deprotection reaction of the N-Boc compound (VI) obtained from the compound (V). A hydroxy group on the 6-side chain of the compound (I) may be protected by alkylsilyl or the like.

The solvation or crystallization of the compound (I) is preferably carried out by dissolving the purified or unpurified compound (I) in a solvent, preferably in a dissoluble solvent and adding timely an indissoluble solvent.

Examples of a dissoluble solvent include alcohols such as methanol, ethanol, ethyleneglycol, methoxyethanol, glycerol and propyleneglycol, ethers such as dioxane, tetrahydrofuran and dimethoxyethan, ketones such as acetone, methyl ethyl ketone and methyl isobutyl ketone, esters such as methyl formate, ethyl formate, propyl formate, methyl acetate, ethyl acetate, propyl acetate, butyl acetate, methyl propionate and ethyl propionate, halogenated hydrocarbons such as dichloromethane, chloroform, carbon tetrachloride, 1,2-dichloroethane, trichloroethane, benzene chloride and dichlorobenzene, nitriles such as acetonitrile and propionitrile, dimethylformamide, dimethylsulfoxide, N-methylpyrrolidinone, quinoline, pyridines and triethylamine. These solvents can be used independently or as a mixture of 2 or more thereof. They can be used with water. Above all, esters, ketones or halogenated hydrocarbons are preferable and esters (e.g., ethyl acetate) are especially preferable.

Examples of an indissoluble solvent include alcohols such as 2-propanol, 2-pentanol, 1-pentanol, t-amyl alcohol, 1-propanol, n-propanol, t-butanol, isobutanol, n-butanol and cyclohexanol, ethers such as diethyl ether, isopropyl ether, dibutyl ether, ethyl isoamyl ether and ethyl phenyl ether, hydrocarbons such as n-pentane, n-hexane, n-heptane, n-octane, n-decane, cyclohexane, methyl cyclo hexane, toluene, benzene, ethylbenzene, cumene, cymene and xylene. These solvents can be used independently or as a mixture of 2 or more thereof. Above all, ethers or alcohols are preferable and alcohols (e.g., 2-propanol, 2-pentanol, 1-pentanol, t-amyl alcohol, 1-propanol) are especially preferable.

The weight ratio of a dissoluble solvent and an indissoluble solvent used in the reaction is usually 1:0 to 1:1000, preferably 1:0.1 to 1:100 and especially preferably 1:1 to 1:50, or usually 0:1 to 1000:1, preferably 0.1:1 to 100:1 and especially preferably 1:1 to 50:1. In a preferable embodiment, ethyl acetate and alcohol are used at a ratio of 1:1 to 15. The total amount of a dissoluble solvent and an indissoluble solvent used in the reaction is usually 0.1 to 1000 weight part per 1 weight part of the compound (I) or the solvate, preferably 1 to 100 weight part and especially preferably 1 to 50 weight part. In another embodiment, a mixture of a dissoluble solvent and an indissoluble solvent can be used.

During the above crystallization, for example, the thermal treatment, the ultrasonication, the stirring or the like is preferably effective to dissolve the compound (I) or the solvate. To the above solution, can be added an indissoluble solvent at a time or continuously immediately before or until the solution becomes muddy. In a preferable embodiment, a proper amount of an indissoluble solvent is added continuously immediately before the solution becomes muddy. A crystal is precipitated usually after an indissoluble solvent is added and the mixture is allowed to stand, and sometimes at the same time that an indissoluble solvent is added. Furthermore, a crystal is sometimes precipitated by cooling the solution. When a crystal is not precipitated by the above method, a crystal can be precipitated, for example, by giving stimulation such as the ultrasonication or the stirring, adding a seed crystal or the like at room temperature or under cooling. The appropriate temperature for crystallizing is about −10 to 40° C. and preferably 0 to 30° C.

A crystal of the compound (I) or the solvate obtained above can be subsequently separated from the solvent by an usual method for separating (for example, filtration, centrifugal separation or the like) and isolated by an usual method for purifying (for example, washing with a dissoluble solvent, an indissoluble solvent or a mixture thereof, or the like). In a preferable embodiment, a crystal is washed with alcohol. A crystal of the compound (I) or the solvate obtained above is of a high purity, therefore the above method for crystallizing can be used to purify a crystal of the compound (I) or the solvate.

The content of residue solvent in a crystal of the compound (I) or the solvate can be changed depending on the method for crystallizing or the degree of drying. The content of residue solvent in the solvate is usually 0 to 5 mole and preferably 0.1 to 1 mole per mole of the compound (I). The solvate may include any dissoluble solvent and any indissoluble solvent described above. The solvent is preferably ethers, esters, alcohols, nitryls or the like and especially preferably alcohols.

(2) A Process for Deprotecting the Compound (I), the Solvate or a Crystal Thereof The compound (II) is a compound in JP1993-294970 and obtained by a deprotection reaction of the compound (I) which has preferably a protected amino group, the solvate or a crystal thereof and preferably a crystal of an alcohol solvate of the compound (I). The deprotection reaction is carried out preferably in nearly 90% yield.

A deprotection reaction (for example, dearylation) is carried out by a well-known method for a person skilled in the art. A catalyst used in this reaction is, for example, a precious metal catalyst such as a nickel catalyst, a cobalt catalyst, an iron catalyst, a copper catalyst, a platinum catalyst or a spalladium catalyst. Preferred is a palladium catalyst, a nickel catalyst or the like and more preferred is tetrakis(triphenylphosphine)palladium, (triphenylphosphine)palladium acetate, (triethylphosphite)palladium acetate or the like. Additives (preferably triphenylphosphine or the like) can be added to the mixed solution with palladium. More preferred is that to a palladium catalyst, is added a reductant for reducing and removing a protecting group or a nucleophilic reagent. Examples of a reductant include hydrogen, metal hydride or the like and preferably tri-n-butyl tin hydride or the like. Examples of a nucleophilic reagent include preferably carboxylate (for example, sodium 2-ethylhexanoate or the like), 1,3-dicarbonyl compound (for example, Meldrum's acid, dimedon, malonic ester or the like) and secondary amine (for example, diethylamine or the like) and more preferably 1,3-dicarbonyl compound (for example, Meldrum's acid).

Any solvent for a usual reaction can be used for a deprotection reaction. The solvent is preferably acetone, acetonitrile, ethyl acetate, dichloromethane, tetrahydrofuran, methanol, ethanol, water or the like and especially preferably acetonitrile. These solvents can be used independently or as a mixture of 2 or more thereof.

A crystal of the compound (I) or the solvate and a nucleophilic reagent are added to a solvent and the reaction system (for example, a reaction mixture and a container) is filled with nitrogen. This reaction can be carried out in the air and preferably under nitrogen stream.

The reaction temperature is about −20 to 50° C. and preferably 0 to 30° C.

The reaction time is usually from a few minutes to several tens of hours and preferably 1 to 3 hours.

In this method for producing, a crystal of the compound (I) or the solvate with a high purity obtained in the above (1) is deprotected, followed by impurities-removing extraction with water and an organic solvent, preferably dichloromethane, to prepare a water solution containing the target compound (II) in a high concentration. As a result, a conventionally essential after-treatment operation such as concentration or column chromatography becomes inessential, resulting in being easy to isolate the target pyrrolidylthio carbapenem derivatives (II), the solvate or a crystal thereof. This method is useful as an industrial method. In this isolation, the target seed crystal is preferably used.

A crystal of the compound (II) or the solvate is preferably a hydrate crystal, more preferably a crystal of type I or type II disclosed in JP2843444 or a crystal of type III (2 hydrate) or type IV (1 hydrate) in WO01/72750. Compared between type III and type IV, a crystal of type IV is preferable because it has a more stability than that of type III. The method for crystallization of each crystal of the compound (II) is described in each document and as below in detail.

A crystal of type III is crystallized from an organic solvent such as alcohol, acetone, acetonitrile or tetrahydrofuran, water or a mixture thereof. Especially preferred is that water is used. Examples of an alcohol include methanol, ethanol, isopropanol and the like. When the mixture of an organic solvent and water is used, the mixed ratio of water/an organic solvent is preferably about 1:0.5 to 1:100 (v/v).

The total amount of a solvent for dissolving is usually 0.1 to 100 weight part per 1 weight part of the compound (II) or the solvate, preferably 1 to 50 weight part and especially preferably 5 to 40 weight part.

To precipitate a crystal from a solution, any operation for precipitating such as cooling and stirring can be carried out. A crystal of the compound is obtained by stirring the solution preferably at a temperature from under cooling to about 10° C.

A crystal separated from the solution is optionally dried. A well-known method for drying is used, for example, drying under reduced pressure by an aspirator or the like. As the drying condition, for example, temperature is preferably about 10 to 50° C., more preferably 15 to 40° C. and most preferably room temperature. Pressure is preferably about 0 to 300 mmHg, more preferably 0 to 100 mmHg, most preferably 0 to 50 mmHg and especially preferably 10 to 40 mmHg. Drying time is, for example, preferably about 1 minute to 1 hour, more preferably 2 to 30 minutes and most preferably 5 to 20 minutes.

A crystal of type IV can be easily obtained preferably by drying the above crystal of type III. The drying is preferably carried out under heating and reduced pressure. For example, temperature is preferably about 20 to 100° C., more preferably 30 to 70° C. and especially preferably 40 to 60° C. Pressure is, for example, 0 to 100 mmHg, preferably 0 to 30 mmHg, more preferably 0 to 20 mmHg and especially preferably 0 to 10 mmHg.

Drying time is, for example, preferably about 1 to 20 hours, more preferably 2 to 15 hours and especially preferably 5 to 10 hours.

A crystal of type IV is preferably isolated as 1 hydrate by drying a crystal of type III of 2 hydrate.

As mentioned above, the present invention provides a crystal of the compound (II) or the solvate with superior stability for preservation and with high industrial utility as an antibiotics.

Examples are shown below to explain the present invention in more detail. However, these examples are not intended to limit the present invention.

Reference Example 1

Enol phosphate (III; 16.20 g, 30.10 mmole) and 2-side chain thiol (IV; 8.44 g, 28.57 mmole) were dissolved in dimethylformamide (48.6 ml). To the solution, was added diisopropylethylamine (6.29 ml) under ice-cooling and the mixture was allowed to stand at 5° C. for 16 hours. The mixture was added to water (250 ml) and the mixture was extracted with ethyl acetate (250 ml, 100 ml). The ethyl acetate layer was washed with water (200 ml) 4 times. The ethyl acetate layers were combined and the solvent was concentrated to give a residue (17.10 g). The residue is subjected to silica gel chromatography (174 g, eluted from n-hexane:ethyl acetate) to give an amorphous compound (I; 8.47 g, 54%).

IR (CHCl$_3$): 1772, 1691, 1410 cm$^{-1}$
$^1$H NMR (CDCl$_3$); δ 1.26 (d, J=7 Hz, 3H), 1.35 (d, J=6 Hz, 3H), 1.70-2.70 (m, 3H), 3.10-3.50 (m, 5H), 3.50-3.80 (m, 1H), 3.90-4.40 (m, 4H), 4.50-4.90 (m, 4H), 5.00-5.50 (m, 5H), 5.80-6.10 (m, 2H)

Reference Example 2

Enol phosphate (III; 14.25 g, 26.47 mmole) and 2-side chain thiol (V; 11 g, 26.47 mmole) were dissolved in dimethylformamide (42 ml). Diisopropylethylamine (5.47 ml, 1.2 eq.) was added thereto under ice-cooling and allowed to stand at 5° C. for 16 hours. The mixture was added to dilute hydrochloric acid (210 ml) and the mixture was extracted with ethyl acetate (120 ml×2). Ethyl acetate layer was washed with water (200 ml) twice. The ethyl acetate layers were combined and the solvent was concentrated to give a residue (20 g). The residue is subjected to silica gel chromatography (200 g, eluted from n-hexane:ethyl acetate) to give an amorphous compound (VI; 8.82 g, 52%).

$^1$H NMR (CDCl$_3$); δ 1.27 (d, J=6.9 Hz, 3H), 1.36 (d, J=6.3 Hz, 3H), 1.48 (s, 9H), 2.55-2.70 (m, 1H), 3.20-3.40 (m, 3H), 3.60-3.70 (m, 2H), 4.00-4.30 (m, 6H), 4.50-4.70 (m, 4H), 4.70-4.90 (m, 2H), 5.25-5.55 (m, 4H), 5.80-6.00 (m, 3H)

Example 1

The results of crystallization of the compound (I) and the solvate by using dissoluble solvents and indissoluble solvents are shown in Table A.

TABLE A

| No | dissoluble solvent | ml | indissoluble solvent | ml | result |
|---|---|---|---|---|---|
| 1 | ethyl acetate | 0.05 | diethyl ether | 0.12 | − |
| 2 | acetone | 0.1 | diethyl ether | 0.2 | − |
| 3 | dichloromethane | 0.1 | diethyl ether | 0.07 | − |
| 4 | acetonitrile | 0.1 | diethyl ether | 0.2 | − |
| 5 | chloroform | 0.1 | diethyl ether | 0.02 | − |
| 6 | tetrahydrofuran | 0.07 | diethyl ether | 0.12 | − |
| 7 | methanol | 0.07 | diethyl ether | 0.25 | − |
| 8 | 2-butanone | 0.1 | toluene | 0.1 | − |
| 9 | methyl acetate | 0.11 | n-hexane | 0.02 | − |
| 10 | ethanol | 0.1 | diethyl ether | 0.28 | − |
| 11 | dioxane | 0.1 | diethyl ether | 0.15 | − |
| 12 | ethyl acetate | 0.06 | 2-propanol | 1 | + |
| 13 | ethyl acetate | 0.02 | 2-propanol | 0.3 | 60 mg+ |
| 14 | dichloromethane | 0.05 | 2-propanol | 0.5 | 38 mg+ |
| 15 | chloroform | 0.03 | 2-propanol | 0.5 | + |
| 16 | acetone | 0.28 | 2-propanol | 0.5 | 44 mg+ |
| 17 | methyl acetate | 0.3 | 2-propanol | 0.5 | + |
| 18 | 2-butanone | 0.3 | 2-propanol | 0.5 | + |
| 19 | isopropyl acetate | 0.3 | 2-propanol | 0.5 | + |

Amorphous powder of the compound (I) (100 mg) was dissolved in a dissoluble solvent and an indissoluble solvent was added thereto continuously immediately before the solution becomes muddy. The solution was stirred at 5-25° C. for several hours to several weeks.

(Result) −: A crystal was not precipitated. +: A crystal was precipitated.

When 2-propanol was used as an indissoluble solvent and ethyl acetate (No. 12, 13), dichloromethane (No. 14), chloroform (No. 15), acetone (No. 16), methyl acetate (No. 17), 2-butanone (No. 18) or isopropyl acetate (No. 19) was used as a dissoluble solvent, a crystal of the compound (I) was precipitated. Especially when ethyl acetate was used as a dissoluble solvent, the crystallinity was the best.

Example 2

Amorphous powder of the compound (I) 200 mg was dissolved in ethyl acetate (1 ml) and the solution was concentrated under reduced pressure to 350 mg. 2-Propanol (4 ml) was added to the residue and the mixture was allowed to stand at room temperature for 16 hours. The precipitated crystal was filtered and washed with 2-propanol. The crystal was air-dried to give a crystal of a 2-propanol solvate 195 mg wherein the content of 2-propanol is 0.5 mole per mole of the compound (I). Differential Thermal Analysis curve: decomposition from 157.4° C.

IR (Nujol): 3529, 3430, 3365, 3218, 3068, 1740, 1712, 1649, 1559, 1456 cm$^{-1}$
$[α]_D^{24° C}$+33.5±0.7° (MeOH, C=1.004%)
$λ_{max}^{MeOH}$ 317.00 nm (ε11,900)
$^1$H NMR (CDCl$_3$); δ 1.21 (d, J=6 Hz, 3H), 1.26 (d, J=6 Hz, 3H), 1.35 (d, J=6 Hz, 3H), 1.90 (br, 0.5H), 2.30-2.40 (m, 1H), 2.50-2.70 (m, 2H), 3.20-3.40 (m, 5H), 3.60-3.70 (m, 1H), 4.00-4.30 (m, 4H), 4.59 (d, J=3 Hz, 2H), 4.60-4.90 (m, 2H), 5.00 (S, 2H), 5.20-5.50 (m, 4H), 5.80-5.90 (m, 1H), 5.90-6.10 (m, 2H)

The signal of NMR for 2-propanol is 1.21 (d, J=6 Hz, 3H), 1.90 (br, 0.5H), indicating that the content of 2-propanol is 0.5 mole per mole of the compound (I). The result of powder X-ray diffraction analysis of the obtained crystal is shown in the above Table 1 and FIG. 1.

Example 3

Amorphous powder of the compound (I; 1.70 g) was dissolved in ethyl acetate (0.9 ml). 2-propanol (17 ml) was added thereto and the mixture was stirred at room temperature for 2 hours. The precipitated crystal was filtered and washed with 2-propanol. The crystal is air-dried to give a crystal of a 2-propanol solvate 1.5 g (88%) wherein the content of 2-propanol was 0.5 mole per mole of the compound (I).

Example 4

A crystal of a 2-propanol solvate (0.5 g, 0.92 mmole) wherein the content of 2-propanol was 0.5 mole per mole of the compound (I) was dissolved in acetonitrile (7.5 ml) and Meldrum's acid (529.8 mg, 3.68 mmole) was added thereto. After degassing and replacing with nitrogen under reduced pressure three times and replacing fully with nitrogen in the reaction container, tetrakis(triphenylphosphine)palladium (318.6 mg, 0.28 mM) was added. The mixture was stirred at room temperature for 1.5 hours. The reaction precipitate was filtered and washed with a mixture of acetonitrile-ethyl acetate to obtain a precipitate (610 mg). To this precipitate, was added water (25 ml) and the mixture was heated at 50° C. After ultrasonic vibration at room temperature, the indissoluble was filtered off and the solution was washed with water. The obtained filtrate was concentrated and purified by chromatography to obtain the compound (II) 340.2 mg (88.0%) from a mixture of methanol-ethyl acetate.

$^1$H NMR (D$_2$O); δ 1.22 (d, J=7.2 Hz, 3H), 1.27 (d, J=6.3 Hz, 3H), 1.64-1.82 (m, 1H), 2.62-2.80 (m, 1H), 3.25-3.59 (m, 5H), 3.63-3.76 (m, 1H), 3.84-4.10 (m, 2H), 4.16-4.29 (m, 2H)

Example 5

To an ion exchange water (360 ml), was added the crude compound (II) (20.0 g) and dissolved under heating to about 50 to 55° C. Under keeping 50° C. and more, this solution was filtrated through a filter which was pre-coated with active carbon (600 mg). The filtrate was cooled to 15 to 20° C. and added a seed crystal (20 mg) of a crystal of type III in WO 01/72750. The mixture was stirred for about 120 minutes to precipitate a crystal, cooled to 0 to 5° C. and aged for 2 hours. 2-Propyl alcohol (200 ml) was added thereto over about 1 hour and the mixture was aged for crystallization at 0 to 5° C. for 2 hours and at the same temperature over night, then a crystal was obtained by filtration. The obtained crystal was washed with 80% 2-propyl alcohol water (40 ml) and dried for about 10 minutes at room temperature under reduced pressure (20 to 30 mmHg) by an aspirator with tap water, to give a crystal of type III (18.1 g, the recovery was 90.5%) compound (II).

Elemental analysis as C$_{15}$H$_{24}$N$_4$O$_6$S$_2$.2H$_2$O

Calcd. (%): C, 39.46; H, 6.18; N, 12.27; S, 14.05.

Found. (%): C, 39.53; H, 6.14; N, 12.40; S, 14.06.

Water Content

Calcd.: (2hydrate): 7.89%.

Measured value by Karl Fischer (KF) titrator: 7.74%

Melting point: 173° C. (decomp.)

Example 6

A crystal of type III (5.0 g) obtained in the above Example 5 was spread in a laboratory dish made of glass and dried at 50° C. under reduced pressure (0 to 5 mmHg) for about 7 hours to give a crystal of IV type of compound (II) (4.8 g, yield 96.0%) disclosed in WO 01/72750.

Elemental analysis as C$_{15}$H$_{24}$N$_4$O$_6$S$_2$.H$_2$O

Calcd. (%): C, 41.08; H, 5.98; N, 12.78; S, 14.62.

Found. (%): C, 41.01; H, 5.92; N, 12.83; S, 14.56.

Water Content

Calcd.: (1hydrate): 4.11%.

Measured value by Karl Fischer (KF) titrator: 4.28%

Melting point: 173° C. (decomp.)

INDUSTRIAL APPLICABILITY

The present invention provides solvates and crystals of synthetic intermediates of carbapenem with superior stability for preservation, superior solubility, and high industrial utility. Additionally, carbapenem antibiotics were obtained efficiently by deprotecting them.

The invention claimed is:

1. A 2-propanol solvate of the compound (I) of the formula:

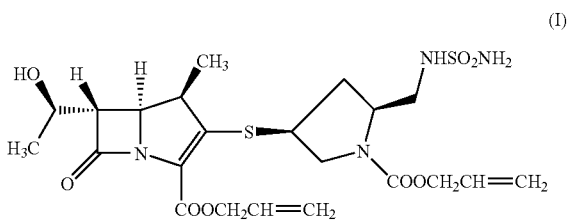

or a crystal thereof.

2. The crystal according to claim 1 wherein the content of 2-propanol is 0.1 to 2 moles per mole of the compound (I).

3. The crystal according to claim 1 wherein the content of 2-propanol is 0.5 mole per mole of the compound (I).

4. The crystal according to claim 1 which has a powder X-ray diffraction pattern using CuK α radiation whose characteristic peaks appear as the spacing (d) of 12.80, 11.21, 4.75, 4.58, 4.28 angstrom.

5. A method for producing the compound according to claim 1 which comprises dissolving the compound (I) or the solvate in a dissoluble solvent and adding an indissoluble solvent thereto;

the dissoluble solvent being selected from methanol, ethanol, ethyleneglycol, methoxyethanol, glycerol, propyleneglycol, dioxane, tetrahydrofuran, dimethoxyethane, acetone, methyl ethyl ketone, methyl isobutyl ketone, methyl formate, ethyl formate, propyl formate, methyl acetate, ethyl acetate, propyl acetate, butyl acetate, methyl propionate, ethyl propionate, dichloromethane, chloroform, carbon tetrachloride, 1,2-dichloroethane, trichloroethane, benzene chloride, dichlorobenzene, acetonitrile, propionitrile, dimethylformamide, dimethylsulfoxide, N-methyl pyrrolidinone, quinoline, pyridine, or a mixture of two or more thereof, optionally in combination with water; and the indissoluble solvent being 2-propanol.

6. The method according to claim 5 which comprises dissolving the compound (I) or the solvate in ethyl acetate and adding the indissoluble solvent thereto.

7. A method for producing the compound (II) of the formula:

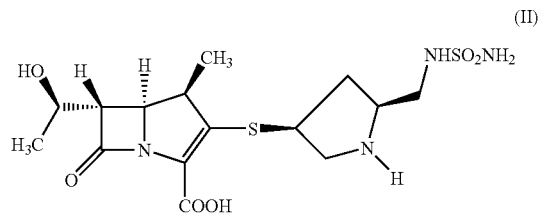

or a solvate or a crystal thereof, comprising deprotecting a solvate of the compound (I) or a crystal thereof according to claim 1.

8. The method according to claim 7, which comprises obtaining a crystal of the compound (I) or the solvate by dissolving the compound (I) or solvate in a dissoluble solvent and adding an indissoluble solvent thereto and deprotecting the crystal;

the dissoluble solvent being selected from methanol, ethanol, ethyleneglycol, methoxyethanol, glycerol, propyleneglycol, dioxane, tetrahydrofuran, dimethoxyethane, acetone, methyl ethyl ketone, methyl isobutyl ketone, methyl formate, ethyl formate, propyl formate, methyl acetate, ethyl acetate, propyl acetate, butyl acetate, methyl propionate, ethyl propionate, dichloromethane, chloroform, carbon tetrachloride, 1,2-dichloroethane, trichloroethane, benzene chloride, dichlorobenzene, acetonitrile, propionitrile, dimethylformamide, dimethylsulfoxide, N-methyl pyrrolidinone, quinoline, pyridine, or a mixture of two or more thereof, optionally in combination with water; and the indissoluble solvent being 2-propanol.

9. The method according to claim 7 wherein a monohydrate crystal of the compound (II) is produced.

\* \* \* \* \*